United States Patent [19]
Shakhnovich et al.

[11] Patent Number: 5,854,992
[45] Date of Patent: Dec. 29, 1998

[54] SYSTEM AND METHOD FOR STRUCTURE-BASED DRUG DESIGN THAT INCLUDES ACCURATE PREDICTION OF BINDING FREE ENERGY

[75] Inventors: Eugene I. Shakhnovich, Lexington; Robert S. DeWitte, Wakefield, both of Mass.

[73] Assignee: President and Fellows of Harvard College, Cambridge, Mass.

[21] Appl. No.: 741,866

[22] Filed: Sep. 26, 1996

[51] Int. Cl.$^6$ ................................................ G06F 19/00
[52] U.S. Cl. .................................. 702/27; 364/578
[58] Field of Search .................................. 364/496, 578, 364/497; 702/19, 27

[56] References Cited

PUBLICATIONS

Klebe, "Toward a More Efficient Handling of Conformational Flexibility in Computer Assisted Modeling of Drug Molecules" Perspectives in Drug Discovery and Design, v. 3, pp. 85–105, 1995.
Wallqvist et al., "Docking Enzyme–Inhibitor Complexes Using a Preference Based Free Energy Surface" Proteins Structure Function and Genetics v. 25, n. 4, pp. 403–419, Aug. 1996.
Guida, W.C.; "Software for Structure–Based Drug Design"; (1994) *Current Opinion in Structural Biology*, Current Biology Ltd., vol. 4: pp. 777–781.
Kasinos et al.; A Robust and Efficient Automated Docking Algorithm for Molecular Recognition: (1992); *Protein Engineering*; vol. 5(1): pp. 69–75.
Kick et al.: "Structure–Based Design and Combinatorial Chemistry Yield Low Nanomolar Inhibitors of Cathepsin D" (1997); *Chemistry & Biology*; vol. 4(4): pp. 297–307 No Month.
Kuntz, I.D.; "Structure–Based Strategies for Drug Design and Discovery"; (1992); *Science*, vol. 257: pp. 1078–1082.
Kuntz et al.; "Structure–Based Molecular Design"; (1994); *American Chemical Society*; vol. 27: pp. 117–123.
Kuhl et al.; "A Combinatorial Algorithm for Calculating Ligand Binding"; (1984); *Journal of Computational Chem.*; vol. 5(1): pp. 24–34.
Lewis et al.; "Automated Site–Directed Drug Design Using Molecular Lattices"; (1992); *Jrnl. Molecular Graphics*; vol. 10; pp. 66–78.
Norel et al.; "Molecular Surface Recognition by a Computer Vision–Based Technique"; (1994); *Protein Engineering*; vol. 7(1): pp. 39–46.
Rotstein et al.; "GroupBuild: A Fragment–Based Method for de Nova Drug Design" (1993); *Jrnl. Med. Chem.*; vol. 36: pp. 1700–1710.
"Molecular Model Drug Design Software Replaces Microscopes with Computers"; (1993); *Genetic Engineering News;* (article).
"Lisa Balbes' Guide to Rational (Computer–Aided) Drug Design" (1992) (Downloaded from Web site).
"Advanced Computational Chemistry Methods for Rational Drug Design" (Downloaded from Web site) No Date, Author.
"Charmm NIH vers. 24 Documentation" (Downloaded from Web site) No Date, Author.

(List continued on next page.)

*Primary Examiner*—Melanie Kemper
*Attorney, Agent, or Firm*—Hale and Dorr LLP

[57] ABSTRACT

A system and method for providing improved de novo structure-based drug design that include a method for more accurately predicting binding free energy. The system and method use a coarse-graining model with corresponding knowledge-based potential data to grow candidate molecules or ligands. In light of the present inventions using the coarse-graining model, the novel growth method of the present invention uses a metropolis Monte Carlo selection process which result in a low energy structure that is not necessarily the lowest energy structure, yet a better candidate can result.

19 Claims, 3 Drawing Sheets

OTHER PUBLICATIONS

"Experimental and Computational Approaches to Structure Based Drug Design, Erice, 9–19 May 1996" (Downloaded from Web site) No Date, Author.

"Molecular Modelling at Harvard" (Downloaded from Web site) No Date, Author.

"Molecular Similarity in Drug Design" (Downloaded from Web site) No Date, Author.

"New Perspectives in Drug Design" (Downloaded from Web site) No Date, Author.

"The NIH Guide to Molecular Modeling" (Downloaded from Web site) No Date, Author.

Blaney, F.; "Molecular Modelling in the Pharmaceutical Industry"; (1990) *Chemistry and Industry;* n.23: pp. 791–794.

Bohm, G.; "New Approaches in Molecular Structure Prediction" (Mar. 1996). *Biophysical Chemistry,* vol. 59 n.1–2:pp. 1–32.

Andrews et al.; "Functional Group Contributions to Drug–Receptor Interactions"; (1984); *Jrnl. Med. Chem.;* vol. 27: pp. 1648–1657.

Bohacek et al.; "Multiple Highly Diverse Structures Complementary to Enzyme Binding Sites: Results of Extensive Application of a de Novo Design Method Incorporating Combinatorial Growth"; (1994); *Jrnl. Am. Chem. Soc.;* vol. 116(13): pp. 5560–5571.

Combs et al.: "Protein Structure–Based Combinatorial Chemistry: Discovery of Non–Peptide Binding Elements to Src SH3 Domain"; (1996) *Jrnl. Am. Chem. Soc.;* vol. 118: pp. 287–288 No Month.

DeWitte et al.; "SMoG: de Novo Design Method Based on Simple, Fast, and Accurate Free Energy Esitmates. 1. Methodology and Supporting Evidence"; (1996); *Jrnl. Am. Chem. Soc.* vol. 118: pp. 11733–11744 No Month.

DeWitte et al.; "SMoG: de Novo Design Method Based on Simple, Fast, and Accurate Free Energy Estimates. 2. Case Studies in Molecular Design"; (1997); *Jrnl. Am. Chem. Soc.* vol. 119: pp. 4608–4617 No Month.

Feng et al.; "Two Binding Orientations for Peptides to the Src SH3 Domain: Development of a General Model for SH3–Ligand Interactions"; (1994); *Science;* vol. 266: pp. 1241–1247.

5,854,992

SYSTEM AND METHOD FOR STRUCTURE-BASED DRUG DESIGN THAT INCLUDES ACCURATE PREDICTION OF BINDING FREE ENERGY

FIELD OF THE INVENTION

The present invention generally relates to systems and methods for de novo structure-based drug design. More specifically, the present invention relates to systems and methods for de novo structure-based drug design that includes a method for accurately predicting the binding free energy in building novel therapeutic molecules or ligands.

BACKGROUND OF THE INVENTION

Finding leads and optimizing the leads that are found are the goals in the development of molecules or ligands that are useful in combating disease and other abnormal body conditions. In recent years, this has involved using, among other things, a molecular similarity method of drug design. This is just one of a number of methods for determining useful leads in the search for new or improved bioactive, therapeutic molecules or ligands. The molecular similarity method of drug design is based on evaluating a large range of chemical structures to find those that show either similarity with each other or complementarity with a biochemical target structure. Chemical structures identified in this manner, usually have a reasonably high probability of binding at the target structure. This search for appropriate chemical structures is enhanced and improved by computer technology which uses search algorithms to search large databases of chemical structures.

Other methods to develop desired leads or ligands has been to use high throughput screening or combinatorial chemistry. These conventional methods have been proven, in certain circumstances, to derive desired leads and ligands.

Structure-based molecular design is yet another method to identify lead molecules for drug design. This method is based on the premise that good inhibitors possess significant structural and chemical complementarity with their target receptors. This design method can create molecules with specific properties that make them conducive for binding to the target site. The molecular structures that are designed by the structure-based design process are meant to interact with biochemical targets, for example, whose three-dimensional structures are known.

The structure-based drug design method has advantages over previous methods. One important advantage is that the structure-based drug design method provides over traditional methods of lead discovery and optimization is an awareness of the intermolecular interactions that are possible.

One goal of the structure-based drug design method is to identify lead molecules. This may be accomplished in a variety of ways. However, the principal generic steps in most structure-based drug design methods are: (1) to identify and determine the structure of the receptor site; (2) to use theoretical principles and experimental data to propose a series of putative ligands that will bind to the receptor sites (which ligands are synthesized and tested for their complementarity); (3) to make a determination of the structure of the receptor/ligand complexes that are successful in binding at low free energy levels; and (4) to iterate steps 2 and 3 in an effort to further enhance binding.

The success of a structure-based drug design method, as can be surmised, may be enhanced through the use of advanced methods of computation which will expedite the identification of key molecular fragments (which may then joined to form molecules) or whole molecules (either from a database of existing compounds or through a molecular growth algorithm). These computational advances enhance the ability to develop molecules or ligands which will successfully bind to macromolecular receptor sites.

One such advance, computational docking of molecules, takes into account the structure of a receptor site and an estimation of the binding affinity of the potential drug design candidate for the macromolecular receptor. This serves as a basis for structure-based drug design through three-dimensional databases of synthesized molecules. There are considerable mathematical challenges that must be addressed and conquered in tackling docking. These include the absence of a clearly best method to mathematically describe the molecular shape of the receptor site and ligand, the packing of the irregular objects together (the receptor and ligand surfaces which are to be joined), and the search issues that are related to graph theory, namely, the study of isomorphic subgraphs to make the matches of a receptor site and ligand.

Docking of ligands has three components: (1) site/ligand description, (2) juxtaposition of the ligand and the site frames of reference, and (3) the evaluation of the complementarity. With regard to the site/ligand description, the atomic coordinates of the receptor macromolecules are obtained through methods, such as X-ray crystallography, nuclear magnetic resonance (NMR), or homology modeling. Site descriptions simply may be the atomic coordinates of the receptor site, however, some notion of the chemical properties of the atoms is needed if there are hopes to measure chemical complementarity, and not just spatial complementarity. Site volume also may be defined if a site boundary is not identifiable. Ligand descriptions closely parallel site descriptions.

Structures for a large number of organic and inorganic compounds have been determined experimentally using X-ray and neutron crystallography technology. If such structures are not so defined, the approximate three-dimensional coordinates for the associated compounds may be obtained by using commercially available computer software products that use a combination of force fields and heuristic rules to generate atomic coordinates.

In considering the juxtaposition of the ligands and receptor sites, the general desire in molecular docking is to obtain the lowest free energy structure for the receptor-ligand complex. Moreover, this search for the lowest free energy selects the best fit at each position of the structure with regard to the lowest binding free energy and selection criteria. To attempt to achieve this result (1) databases of putative ligands are searched and identified ligands are ranked according to their respective interactive energies with a particular receptor site and (2) computational studies are made of the geometry of particular complexes.

In evaluating the complementarity of a receptor site and ligand, of interest for ligand design is the free energy of binding ($\Delta g_{binding}$). This may be calculated directly using free energy perturbation methods, if an accurate geometric model of the ligand-receptor complex is available. Free energy calculations generally require a great deal of computational time, i.e., in the order of days. In light of this, there have been many proposed simplifications for calculating free energy; however, these simplifications have tended to add to the inaccuracy of the free energy determination. This degradation of the accuracy is unacceptable, and, as such, is there is a demand for a method to compute free energy in what is considered a reasonable amount of time, which is in the minute or less range, and accuracy does not suffer.

The calculation or prediction of free energy can be effected by any of a number of commercially available software programs. A few of these programs and their computational strategies will be discussed in greater detail subsequently.

It is known to use one of two methods to automatically search databases that contain large amounts of data relating to fragments that can be used for building molecules or ligands for developing lead candidates. A first method is the Geometric method that matches ligand and receptor site descriptors. A second method is to align the ligand and receptor by minimizing the ligand and receptor interactive energy. To fulfill the requirements of this method, energy-driven searching may be based on molecular dynamics ("MD") and traditional Monte Carlo ("MC") simulations. These methods, however, require a tremendous amount of computational time. Finding the lowest energy state of a given ligand-receptor complex using either of these methods is a fundamental problem.

Attempts to find ways around the actual calculation of free-binding energy has resulted in search methods based on descriptors, grids, and fragments. Looking to descriptor matching methods, an analysis is made of the proposed receptor region at which binding is to take place. Ligand atoms are then positioned at the best locations at the site. This gives an approximated ligand-receptor configuration that may then be refined by optimization. Descriptor matching methods are reasonably fast and provide a good sampling of the region of interest at the receptor site. Many of the descriptor matching methods use algorithms that employ combinational search strategies. As such, small changes in parameter values can cause the computational time required to become unreasonable long.

DOCK is one of the earliest descriptor matching programs. DOCK software was developed at the University of California at San Francisco and provides a method that attempts to solve the problem by developing a drug by creating a negative image of the target site, searching a database for a similar ligand, placing putative ligands into the site, and evaluating the quality of the fit.

In using the DOCK software, an important factor is the accurate prediction of binding free energy. In favorable cases, the accuracy can reach as high as 1–2 kcal/mol. In operation, DOCK uses spheres locally complementary to the receptor surface to create a space-filling negative image of the receptor site. Several ligand atoms are matched with receptor spheres to generate chiral orientations of the ligand in the site. Databases of small molecules are searched for candidates that complement the structure of the receptor site.

There are problems with DOCK which result in predictions that are, in fact, not as accurate as desired. Further, DOCK is unable to suggest any novel structures, it can only search for what is in a database.

CAVEAT software, also a descriptor matching method, is based on directional characterization of ligands. CAVEAT was developed at the University of California at Berkley. This program searches for ligands with atoms located along specified vectors. The vectors are derived from structural information from known complexes. CAVEAT focuses on searching ligand databases to find templates as starting points for chemical structures.

FOUNDATION software provides a descriptor matching method that attempts to combine models of crucial ligand atoms and structure-based models. In using FOUNDATION, the searcher identifies atom and binding types that the candidate molecule must possess. FOUNDATION relies heavily on the detailed atom-type, bond-type, chain length, and topology constraints provided by the searcher to restrict the search. FOUNDATION only considers the steric component of the active site and relies on the matching information to find chemically complementary ligands. The tight constraints that are required by the FOUNDATION program restrict the candidates to one orientation at the receptor site.

CLIX software, developed at CSIRO, an Australian company, resembles DOCK by using the receptor site to define possible binding configurations. CLIX relies on an elaborate chemical description of the receptor site. This program uses fewer receptor-ligand matches than does DOCK. CLIX also evaluates interaction energies at the receptor sites.

Grid search methods are used to sample the six degrees of freedom of the orientation space. These methods identify an approximate solution, which cannot be guaranteed with discrete sampling methods. Accuracy is limited by the step size used in the search of the various positions. The size of step also determines the time of the search, i.e., the greater the number of incremental steps, the greater the search time. Methods that use additional sampling in regions of high complementarity can overcome this problem.

A first type of grid search method is a side chain spheres method. This method explores protein-protein complexes using simplified sphere representations of side chain atoms and a grid search of four rigid degrees of freedom. This program uses surface evaluation algorithms, full molecular force-field evaluations of complexes, and simulated annealing to refine initial docking structures.

A second type of grid search method is a soft docking method. According to this method, receptor and ligand surfaces are divided into cubes to generate the translational part of the search. A pure rotational grid search is conducted on the sample ligand at orientations in discreet angular increments. The accuracy is limited by size. Run-time scaling is the cube of the rotational step size and is a product of the number of the receptor-ligand surface points.

Fragment-joining methods identify regions of high complementarity by docking functional groups independently into receptors. These methods are not particularly bothered by rigid ligand issues because of the added combinational search. Fragment-joining methods suggest unsynthesized compounds, but connecting the fragments in sensible, synthetically accessible patterns is difficult. Fragment-joining methods have the problem that there is a need to connect functional groups to form complete molecules while maintaining the fragments at the geometric positions of lowest energy.

GROW is a fragment-joining method which has been used to design peptides complementary to proteins of a known structure. The software was developed at Upjohn Laboratories, Kalamazoo, Mich. In operation, a seed amino acid is placed in the receptor site followed by iterative additions of amino acids. Conformations are chosen from a library of precalculated low-energy forms. At each addition of a peptide, the peptide-receptor complex is minimized and evaluated. Only the best 10–100 low energy structures are kept at any stage.

HOOK, developed at Harvard University, Cambridge, Mass., is a fragment-joining method that finds hot spots in receptor sites by looking for low energy locations for functional groups. HOOK uses random placement of many copies of several functional fragments followed by molecular dynamics.

Multiple Start Monte Carlo methods also have been used as fragment-joining methods. These methods conduct searches of databases for fragments of a ligand to dock at the receptor site.

BUILDER software, uses a family of docked structures to provide an irregular lattice of controllable density. This lattice can be searched for paths that link molecular fragments.

LUDI is a fragment-joining method that proposes inhibitors by connecting fragments that dock into microsites on the receptor. LUDI was developed at BASF, Stuttgart, Germany. The fragments are from a predetermined list of molecular fragments. The microsites are defined by hydrogen bonding and hydrophobic groups. Ligand pseudoatom positions are generated within microsites on the basis of an appropriate angle and distance minima for various interactions. The fragments identified are connected using linear chains composed of one or more of 12 functional groups.

GRID software is a hybrid grid/fragment-joining method that places small fragment probes at many regularly spaced grid points within an active receptor site. This program, developed at Oxford University, England, has been found to reproduce the positions of important hydrogen bonding groups. GRID uses empirical hydrogen bonding interaction potential and spherical representations of functional groups to generate affinity contours for various molecular fragments. This identifies regions of high and low affinity. The contours may be used to guide chemical intuition or as an input for other analysis programs. GRID is limited by its representation of the fragments since it does not allow prediction of fragment orientation.

To obtain accurate results from the programs discussed above, there is a need to understand, evaluate, and predict (or calculate) the binding free energy at the receptor sites. There also is a need to do so in a reasonable amount of computational time. The current predictive and short cut calculation methods leave much to be desired for improving structure-based drug design.

The prediction of binding free energy is according to the Expression:

$$\Delta g_{binding} = \Delta e_{binding} - T\Delta s_{binding} \quad (1)$$
$$= \Delta e_{complex-formation} - T\Delta s_{complex-formation} +$$
$$\Delta e_{solvation-desolvation} - T\Delta s_{solvation-desolvation}$$

where, $\Delta g_{binding}$=The total binding free energy for a protein-ligand complex.

$\Delta e_{binding}$=The interaction energy minus any intramolecular strain induced on complex formation.

$\Delta s_{binding}$=The change in conformational freedom induced by the formation of the complex.

$\Delta e_{complex\ formation}$=The interaction energy for the ligand/protein complex.

$T\Delta s_{complex\ formation}$=The change in entropy due to the reduction in flexibility in both the ligand and the protein upon complex formation.

$\Delta e_{solvation-desolvation}$=The energies of solvation are the energetic factors from the transfer of hydrophilic and lipophilic groups from an aqueous solvent to the more lipophilic region of the protein binding site.

$\Delta s_{solvation-desolvation}$=The entropy of solvation relating to the changes in the order of the solvent at the interface between ligand and solvent, and the protein and solvent on complex formation.

The ability to rapidly and accurately compute binding affinity of ligands for macromolecular receptors remains a problem in de novo structure-based drug design. Even though free energy perturbation calculations can produce relative binding free energies to within 1 kcal/mol, these methods are limited. The CPU ("Central Processing Unit") time required to ensure convergence is excessive even using the fastest computers and the method is confined to small mutations between that pair of molecules for which there is an attempt to compute the difference in binding free energy.

To emphasize this point, in de novo structure-based drug design, there is the need to be able to test as many molecules as possible at proposed receptor sites in a short period of time and rank the tested structures based on an accurate prediction of the binding free energy. If small organic molecules are thought of as simple combinations of functional groups, candidate molecules may be considered as a choice and an arrangement, for example, of five functional groups. As such, a database of fragments that is being used to construct such a small organic molecules can result in an extremely large number of structures that must be evaluated. For example, even a very small database of 50 fragments will produce nearly 1 billion candidates of 5 functional groups—$50^5$ combinations. As the size of the database of molecular fragments increases, it is readily seen that the number of possible combinations will increase dramatically. As such, the computational time necessary to test every combination, using current technology, is unreasonable and, therefore, not practical. The present invention provides a system and method that enhances the ability to conduct searches. In particular, a quick and accurate free energy estimation method is used for testing only the most meaningful combinations.

Conventional computational methods, such as those already discussed, use algorithms that hopefully overcome some of the computational burdens. However, in attempting to overcome the computational burdens, accuracy in predicting the binding free energy, which is a very important parameter to know in ranking possible candidates, has suffered greatly. For accurate estimates of binding free energy, sophisticated simulations using empirical potential and stepwise estimation of the changes in enthalpy and entropy at each stage of the thermodynamic cycle have been used to calculate the free binding energy. These calculations require extensive computational time for each molecule, which is impractical for normal structure-based drug design. These conventional methods, therefore, use scoring techniques that provide a short list of possible candidates for complete thermodynamic determination, or chemical synthesis and experimental determination of binding free energy.

In many of the methods for approximating the full expression for binding free energy, the scoring is based solely on the interaction energy between the ligand and protein in the complex as the single most important contributor to free energy. In others, ranking may be based more on spacial complementarity than chemical complementarity. In these cases, the solvation contributions are taken as being an approximation of the surface area. In either of these two methods the scoring is incomplete, which adversely affects the accuracy of the rankings of the candidate molecules or ligands.

In de novo structure-based drug design, there have been a number of methods to try to generate and rank lead candidates for docking at receptor sites. In the past, however, accuracy in predicting free energy suffered when short-cut methods were used to determine binding free energy. Therefore, unless excessive computational time was used to calculate the binding free energy in a three-dimensional protein-ligand complex, there will be a great chance of inaccuracy. Since the ranking of candidates molecules and ligands is primarily based on binding free energy, the chance of improperly ranking the candidates is very high.

The computational time needed for sampling a large number and variations of structures to generate potential lead candidates is usually very large and unreasonable. Since it is highly desirable to sample as many structures in as short a period of time as possible and then rank them based on accurate prediction of their binding free energy, there has been a need for a system and method to grow lead molecules without the computational burden of the past but with greater accuracy in binding free energy prediction.

SUMMARY OF THE INVENTION

The present invention is a system and method for computational de novo structure-based drug design that employs a novel method for discovery and building ligands, and a more accurate method for predicting binding free energy. Accordingly, the system and method of the present invention provide a better predictive de novo structure-based drug design tool by using a coarse-graining model with corresponding knowledge-based potential data. Moreover, in light of the use of the coarse-gaining model, the novel molecular growth method of the present invention uses a metropolis Monte Carlo selection process for molecule growth that builds the molecules or ligands that result in a low free energy structure, but not necessarily the lowest free energy structure, yet such a structure that is grown has a more accurate prediction of binding free energy and can be an acceptable drug design candidate.

The molecular growth method of the present invention uses the Metropolis Monte Carlo method to quickly search and sample the configuration space of the binding site. The is done with knowledge of the interactive potential for the fragments that are part of a database. The Metropolis Monte Carlo method also gives the system and method of the present invention the ability to identify very quickly fragments that will be useful in building the molecules or ligands.

The coarse-graining model with knowledge-based potential data follows from the application of the principles of canonical statistical mechanics to subsets of proteins, in particular the determination that small subsets of a folded protein are in thermal equilibrium with each other. As such, the present invention employs these principles. Thus, there is a reasonable basis to contend that the information present in the crystal structures of proteins and crystal structures of protein-ligand complexes may be disassembled into constituent parts and the contribution of each part to the binding free energy may be assigned on the basis of probability. The permits the present invention to achieve the more accurate results for binding free energy predictions and apply them in building the molecules or ligands.

According to the system and method of the present invention, the identification of candidate molecules is not just a search for the lowest free energy complex, but is a search to identify candidate molecules or ligands that form low free energy complexes at the receptor site but give the best lead for drug design. This is accomplished using the growth method that employs a metropolis Monte Carlo selection process. The molecular growth method results in low free energy candidates generated of a desired length.

An object of the present invention is to provide a novel system and method for structure-based drug design.

Another object of the present invention is to provide a novel system and method for structure-based drug design that has a more accurate method for predicting the binding free energy at the protein-ligand complex.

A yet further object of the present invention is to provide a novel system and method for building candidate molecules or ligands for binding at a receptor site that uses a more accurate method for predicting binding free energy at the protein-ligand complex.

These and other objects will be described in greater detail in the remainder of the specification referring to the drawings.

DETAILED DESCRIPTION OF THE INVENTION

The present invention is a system and method for structure-based drug design that uses a novel method for building candidate molecules or ligands, which employs a more accurate method to predict the binding free energy of the molecules or ligands as they are grown. The system and method of the present invention also grows candidate molecules or ligands in which there is a more accurate prediction of the binding free energy in a reasonable amount of computational time.

Unless indicated otherwise, the following definitions will apply in describing the present invention:

Binding is a physical event in which a ligand is associated with a receptor site in a stable configuration.

Docking is a computational procedure whose goal is to determine the configuration that will permit binding.

De novo structure-based drug design is meant to refer to a process of dynamically forming a molecule or ligand which is conducive to binding with a particular receptor site using knowledge of the protein structure.

Ligand is a molecule that will bind with a receptor at a specific site.

Molecule (in the context of structure-based drug design) is a structure true that can be formed based on the proposed receptor site.

Interaction radius is the distance within which an interaction of protein and ligand atoms must take place.

Reference state is an artificial configuration of ligand and protein atoms in which the frequency of all interaction types is exactly average. It is best described by the average probability $\bar{p}=<p_{ij}>$.

Quasichemical approximation is a mathematical method for converting probabilities to energies based on the principles of canonical statistical mechanics.

Figure 1:
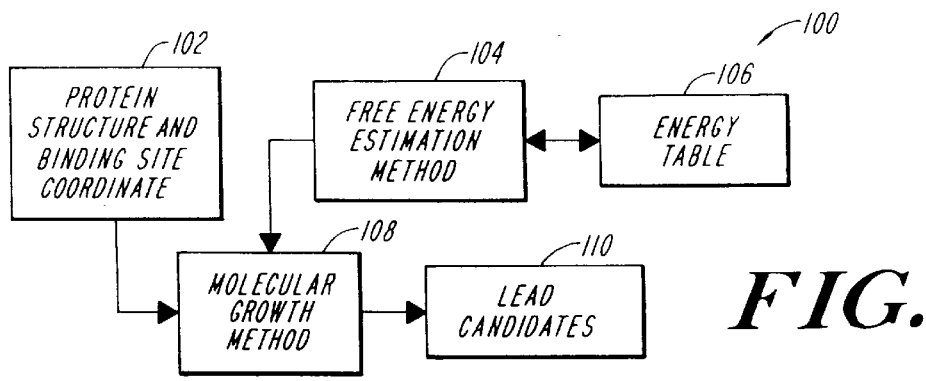
FIG. 1 shows a block diagram of the method employed by the system of the present invention.

Referring to FIG. 1, generally at 100, the novel method that the system of the present invention uses for building and ranking lead candidates for de novo structure-based drug design, as shown. In FIG. 1, molecular growth method 108 receives inputs from 102 and 104. At 104, information regarding the protein structure and its binding site is provided. With regard to the binding site, at least one coordinate is provided to identify a proposed receptor site. The free energy estimate method at 104 provides the estimate of free energy of the molecule or ligand that is being built. The free energy method receives input from energy table 106 which is developed according to FIG. 3, which will be described subsequently. Once a number of molecules or ligands have been built, they are ranked at 110, usually based on their binding free energy, as lead candidates for drug design.

In a little greater detail, at 102, information about the protein structure that includes the binding site is provided to molecular growth method 108. This information includes the coordinate of the binding site, protein atom coordinates, and protein atom types in a standard Brookhaven Protein Data Bank ("PDB") format or notation.

The second input to molecular growth method 108 is the free energy estimate for the molecule being built. As stated, this free energy estimate method uses the information from the calculated free energy database developed according to FIG. 3. This prediction is based on proper selection of an interaction model and reference state, selection of an appropriate interaction radius, knowledge of the atom types at issue, information with regard to known structures of protein-ligand complexes (knowledge-based potential data), and quasichemical approximations.

The molecular growth method at 108 is set forth in detail in FIG. 2, generally at 200, and will be described subsequently. This method employs a Metropolis Monte Carlo ("MMC") selection process to control the acceptance of intermediate and finished molecules or ligands as conditions based on their estimated binding free energy.

Figure 2:
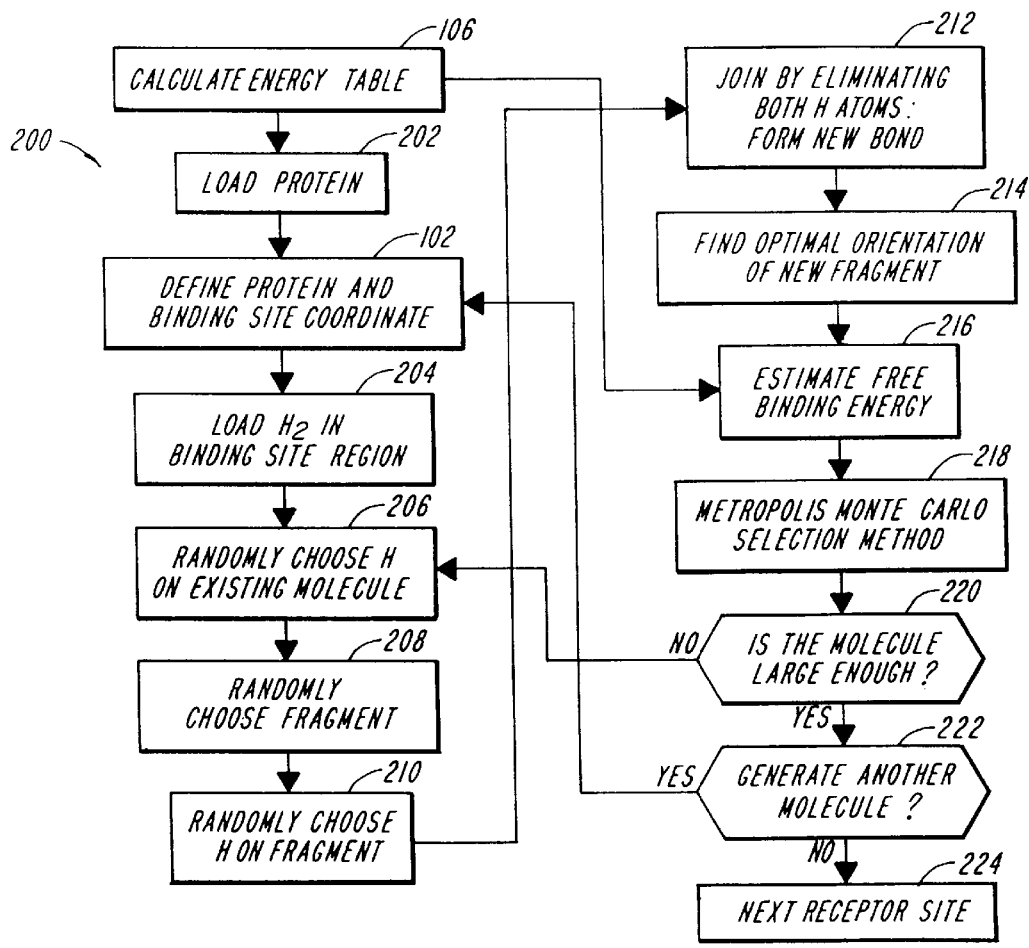
FIG. 2 is a block diagram for the method of estimating binding free energy that may be used in the molecule growth method employed by the system of the present invention.

Referring to FIGS. 1 and 2, the molecular growth method at 108 will be discussed in detail. At 106 in FIG. 2, the energy table (based on FIG. 3) is calculated. This table is calculated once for a given set of parameters. When the parameters are changed, the table is recalculated. For example, if the interaction radius is changed from 5 Å to 3 Å, the table may be recalculated. It is necessary to calculate the table at or near the beginning of the method of the present invention so that it may be accessed in building molecules or ligands.

At 202 in FIG. 2, the protein with a target receptor site is loaded. This is followed by step 102 at which the information about the protein that has the target receptor is input from 108 of FIG. 1. This information describes the protein structure and the binding site at issue. In describing the binding site, its relative position is given in the form of a coordinate. From this point, the molecular growth method will grow a molecule or ligand that is a simple organic molecule which consists of fragments joined with single bonds.

At 204, a hydrogen molecule ("$H_2$") is positioned randomly in the binding site of the protein at the coordinate. This $H_2$ molecule is considered to be the existing molecule to satisfy step 206. According to step 206, one of the H atoms is randomly selected to be the site of the new bond.

Step 208 is performed by selecting at random a fragment from a library of fragments. For example, a library could include the fragment set forth in Table 1:

TABLE 1

Fragments For Molecule Growth Method

| | | | |
|---|---|---|---|
| 1. amide | 14. cyclohexane | 27. indole | 39. purine |
| 2. amine | 15. cyclohexane | 28. iodide | 40. pyramidine |
| 3. carbonyl | 16. cyclohexane | 29. methyl | 41. pyradine |
| 4. carboxylic acid | 17. cyclohexene | 30. n-butyl | 42. pyrrole |
| 5. chloride | 18. 1,2-dithian | 32. naphalene | 43. sulfate |
| 6. cyanide | 19. ethane | 33. nitrile | 44. sulfide |
| 7. cyclo-octane | 20. ethene | 34. nitro | 45. t-butyl |
| 8. cyclo-octane(2) | 21. fluoride | 35. phenyl | 46. tetrahydrofuranyl |
| 9. cyclo-octane(3) | 22. furan | 36. phosphate | 47. tetrahydrothienyl |
| 10. cyclo-pentane | 24. glucose | 37. propane | 48. thiophene |
| 11. cycloheptane | 26. hydroxyl | 38. propene | 49. trifluoromethyl |

At step 210, there is the random selection of at lest one H atom on the randomly selected fragment. The selected H atom from the $H_2$ molecule and the H atom from the fragment will form the first fragment bond for the molecule being built at the protein binding site.

At step 212, the first (and new) bond is formed between the first fragment and the remaining H atom from the $H_2$ molecule loaded at step 204. As this bond is formed, the two H atoms that were selected are eliminated. By following the method of the present invention, it is assured that the new bond angles and bond lengths are reasonable.

The next step is at 214 where the new fragment is oriented with respect to the bond just created and binding site by torsional rotation about the new bond so that the new fragment is properly situated at the binding site at a low energy level. Preferably in orienting the new fragment by torsional rotation about the new bond, the orientation is performed in fixed increments. These fixed increments are the smallest that will still permit reasonable computational times. Orientations that are not sterically hindered are evaluated for their free energy value at step 216. The position of the fragment or rotamer that yields low energy or the lowest energy is considered as a candidate for the molecule that is being grown.

Using the molecular growth method of the present invention, it is found that molecules or ligands of any desired size may be built. This is realized by the ability to add fragments by the displacement of H atoms and binding of the atoms that were formerly connected to the displaced H atoms. The branching effect is fully realized in that any H atom of the structure that is attached to the protein is a potential growth site.

Figure 3:
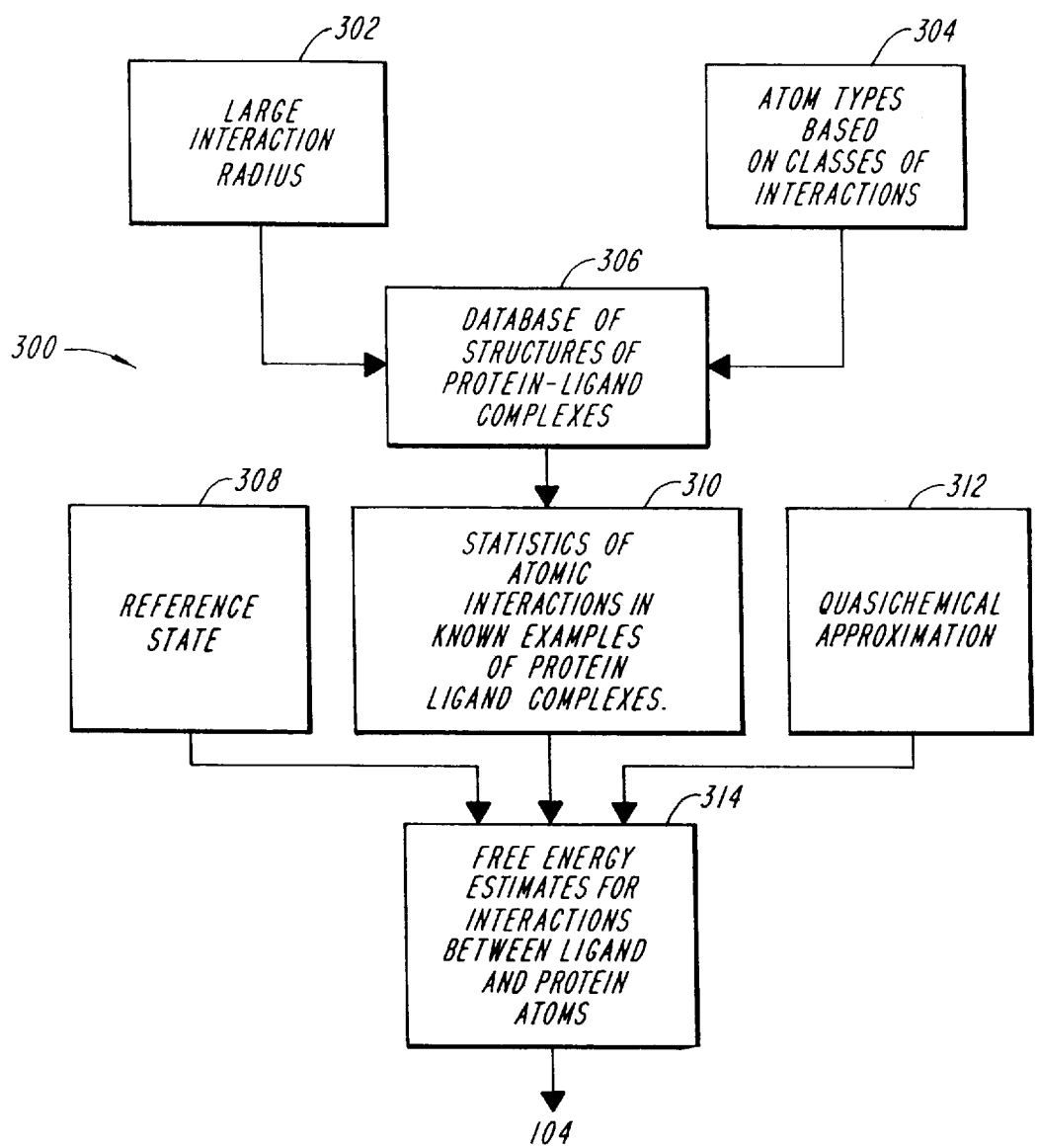
FIG. 3 is a flow diagram of the molecular growth method of the system of the present invention.

At 216, there is the prediction of free energy for the molecule being built. The method of estimating free energy is shown in detail in FIG. 3 at 300. FIG. 3 is a block diagram of the method for creating or calculating the energy table that is used to provide the desired free energy information for the molecule that is being grown fragment by fragment. In order to understand what is being estimated, it is necessary to understand the factors that determine the binding free energy of molecules. The remainder of the molecular growth method will be discussed before the method of estimating binding free energy is discussed in detail.

After step 216, the molecular growth method advances to step 218. Using a coarse-graining model with knowledge-based potential data, the system and method of the present invention evaluates the combinatorial search space, (the binding site of the protein), which is a rough energy landscape, to develop and identify candidate lead molecules that have a low, not the lowest, free energy complex. The system and method of the present invention overcome the multiple minimum problem, by using a MMC selection process at step 218. In order to determine whether this fragment will be accepted as a condition, once the binding free energy has been computed for each of the orientation of the rotamer, the MMC selection process at 218 makes a comparison with respect to the energy per atom before the current growth step and after the growth step at the optimal orientation. If there is a decrease in the energy per atom with the new built step, then that orientation is accepted as a condition. If an increase in energy per atom is experienced, however, it also is accepted as a condition but with a probability defined by Example (2):

$$p = \exp\left[-\frac{\Delta g}{T}\right] \quad (2)$$

where,
p=Probability of acceptance.
$\Delta g = \Delta G/N$ is the change in free energy per atom (with $\Delta G$ being the free energy difference upon adding the fragment at issue and N being the total number of atoms in the ligand).
T=Temperature.

The MMC selection process according to the system and method of the present invention allows the energy per atom to increase occasionally. This is needed if a small molecule is grown into a tight steric region of the binding site and the molecule had to be grown into the solvent or other unoccupied region and only marginally interact with the protein was present. Thus, allowing such an increase may provide an opportunity for a subsequent larger decrease in the free energy of binding.

Using the MMC selection process of the present invention as an optimization method has advantages. This method creates a low energy molecule in light of the random selection of rotamers that does not lead to significantly more metropolis failures. Further, the method will indirectly result in the tightest possible steric complementarity.

The step at 220 is to determine if the molecule that has been built is large enough at this point in time. If it is, then the method is directed to step 222. At step 222, it is determined if another molecule is to be built at this same binding site of the protein. If no additional molecules are built, the method will cease generating molecules for this protein binding site and the method will go to step 230 to wait for a next protein for which a candidate molecule or ligand is to be built. If the answer at step 222 is "yes" and another molecule is to be generated, then the method is directed back to step 204 where $H_2$ is added to the binding site of the protein where the new molecule or ligand is to be built.

If at 220 it is determined that the molecule is not large enough, then the method of the present invention returns to step 206 where another fragment is randomly selected for the addition to the existing molecule in the described manner.

In performing the method of the system of the present invention, consideration is given to the parameters surrounding performance of the method. Some of the parameters that are considered are the temperature at which the building takes place, the nearest approach allowed between atoms when assessing steric hindrance, and the angular increment in choosing fragment rotamers.

Preferably, the temperature that is selected is one that generates the largest number of low energy structures per unit of time. The nearest approach of two atoms is a percentage of the sum of their van der Waal radii since this will provide a good correlation with the nearest approaches in the database. The selected incremental amount for torsional orientation of the fragments can be further refined to smaller increments. However, such smaller increments may result in significantly more computational time to obtain results. Given the preferred parameters a molecule of at least twenty heavy atoms can be generated in about one second.

The method for estimating binding free energy will now be discussed in detail referring to FIG. 3. As stated, Expression (1) is used to estimating binding free energy:

$$\begin{aligned}\Delta g_{binding} &= \Delta e_{binding} - T\Delta s_{binding} \quad (1) \\ &= \Delta e_{complex\_formation} - T\Delta s_{complex\_formation} + \\ & \quad \Delta e_{solvation\_desolvation} - T\Delta s_{solvation\_desolvation}\end{aligned}$$

Again, referring to FIG. 3, in estimating the binding free energy that will be part of the energy table, the items at 302 and 304 are combined with the items at 306 to generate the statistics of atomic interactions of known protein-ligand complexes, which is shown at 310. The information at 310 forms the knowledge-based potential interaction data that is used for estimating binding free energy of particular molecule being built.

At 302, a large interaction radius for the atoms that are to be bound in the protein-ligand complex is selected. A large interaction radius is selected because it will permit the solvation entropy effects to be accounted for. The most feasible length is selected for the interaction radius.

At 304, information is provided regarding the atom types based on the different classes of possible interaction. Table 2 provides examples of information that is included at 304:

TABLE 2

| Atom-type Interaction Data | | |
|---|---|---|
| Description | Atom Type | Code |
| Lipophilic Carbon Atoms | Fatty Carbon | CF |
| Oxygen That Accepts Hydrogen Bonds | Oxygen Acceptor | OA |

Item 306, therefore, includes at least information about the atom-types that are suspected will be present at the protein-ligand complex.

Now referring to the database at 306, this database includes a listing of structures of protein-ligand complexes that are known, their coordinates, and corresponding chemical elements. This database is one that can be continually updated as more information is obtained. A sample of the information that is in this database is shown in Table 3:

TABLE 3

Protein-Ligand Complex Database

| Protein | PDB Code |
|---|---|
| Purine Nucleoside Phosphorylase | 1 PNP |
| Amino Acid Binding Protein | 1 LST |

The information from 302 and 304 when combined with information at 306 result in the knowledged-based data at 310. Specifically, the information at 310 is the statistics of atomic interactions in known protein-ligand complexes which will permit a more accurate prediction of binding free energy for the molecule or ligand being built.

The next issue is to compile the statistics at 310 into a set of interaction parameters that constitute the free energy contribution of interactions between specific atom types. Given the probability of atomic interactions in known protein-ligand complexes from 310, this information, along with reference state for the molecule or ligand being built, are combined. This reference state is selected such that it accounts for the solvent energy and configuration entropy effects.

The third item that is combined to generate the estimate from binding energy is the quasichemical approximation of the protein-ligand complex of the molecule or ligand being built that is at 312.

When the information from 308, 310, and 312 is combined, the results is the energy table at 106 that is used to provide the estimated free energy contributions for each type of interaction possible for the molecule or ligand being built. An example of the data provided in the free energy table at 106 is shown in Table 4:

TABLE 4

Energy Tables

| Protein Atom | Ligand Atom | Δgij |
|---|---|---|
| CF | CF | −2.18 |
| CF | OA | −1.13 |
| OA | CF | −0.89 |

Figure 4:
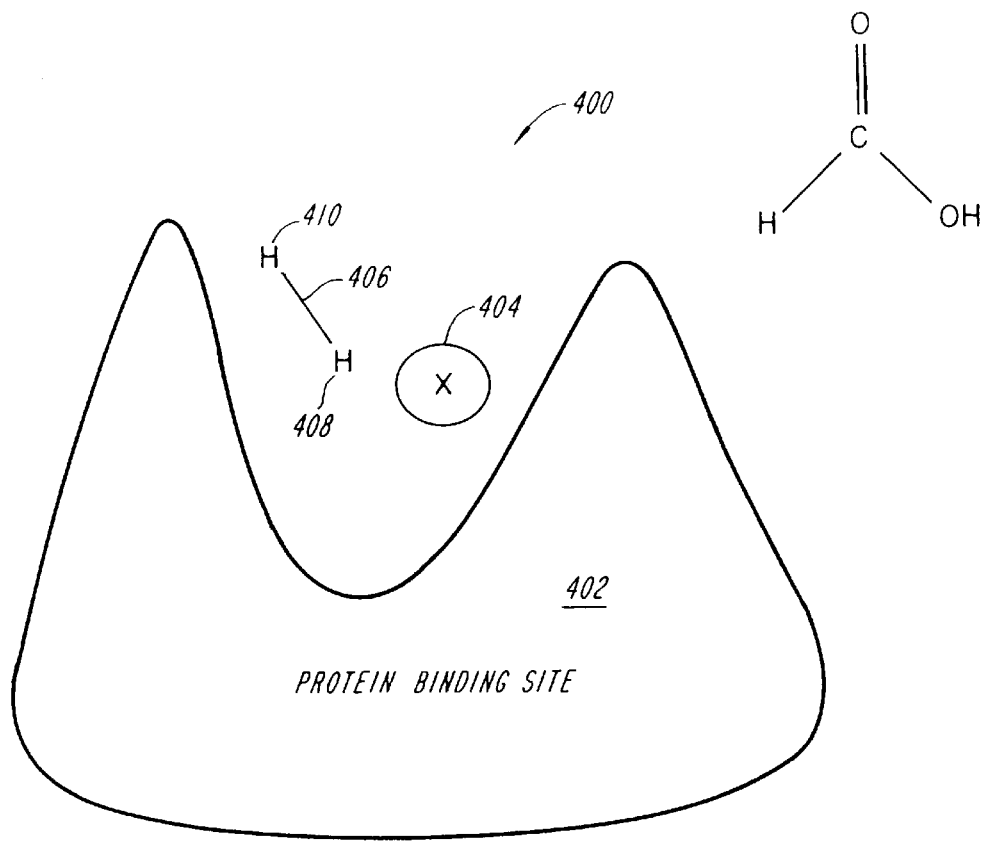
FIG. 4 shows an example of a protein receptor site with at least an $H_2$ molecule loaded in it.

Before discussing the statistical support for the present invention, FIGS. 4 and 5 will be described. Those Figures graphically demonstrate aspects of FIGS. 1, 2, and 3. Referring to FIGS. 2 and 4, when protein 402, shown generally at 400, is loaded, it is defined and the coordinate of the binding site, such as coordinate "X" at 404, is determined. Next $H_2$ molecules, such as $H_2$ molecule 406, is added to the binding site. As would be understood, more than one $H_2$ molecule may be added to a single binding site.

After the $H_2$ molecule is loaded in the binding site, either H atom 408 or 410 is selected for forming the new bond. In this case, H atom 410 is selected. Once the selection is made, a fragment is randomly chosen from the fragment library and an H atom of that fragment is selected for establishing the new bond.

Figure 5:
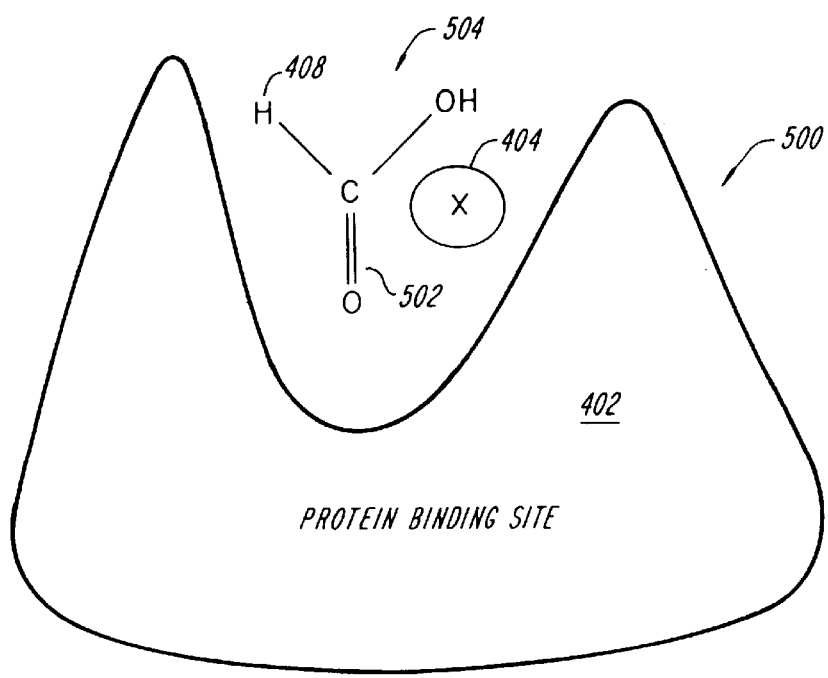
FIG. 5 shows an example of a protein receptor site with a molecule being built in it.

Referring to FIGS. 2 and FIG. 5, generally at 500, one H atom of fragment 502 is selected for forming the first bond. When this bond is formed, the selected H atoms of $H_2$ molecule 406 (FIG. 4) and fragment 502 are eliminated. When new bond 504 is formed, the first fragment has been added in building the molecule.

The added fragment is now incrementally rotated about bond 504 to obtain the best fit and the free energy estimation is made based on the different orientations. An evaluation of the new molecule is made based on the MMC selection method described previously, then the remainder of the method of FIG. 2 is carried out.

As stated, the present invention, implements a coarse-graining model with corresponding knowledge-based potential data. This model is used because of the ability to apply the principles of canonical mechanics to subsets of folded proteins that are in thermal equilibrium with one another. As such, the crystal structures of proteins and crystal structures of protein-ligand complexes may be disassembled into constituent parts. The contribution of each part may then be assigned on the basis of probability.

Generally, in statistical mechanics any two states at the same energy have an equal probability of the occupation of a location. This is expressed in Expression (3):

$$p^e_{ij} = \frac{\exp\left[-\frac{e_{ij}}{kT_e}\right]}{Z} \quad (3)$$

where, $p^e_{ij}$=The energetic probability of an interaction between a protein atom of type i and ligand atom of type j.

$e_{ij}$=The energy of the interaction of a protein atom of type i and ligand atom of type j.

k=Boltzmann Constant.

$T_e$=Experimental temperature at which the data base information is obtained.

Z=Normalization Constant.

In forming protein-ligand complexes, configurations that have exactly the same energy are not equally likely to be formed. This is because of the strong presence of a boundary in the space sampled by the ligand. The entropic effects are solvent ordering and restrictions on the atomic interactions due to steric hindrance and the fixed chemical structures of the protein and ligand. The entropic effects are not correlated to the energetic events, and, therefore, may be expressed as the sampling probability $p^s$, which relates to the entropic effects, as set forth in Expression (4):

$$p^s_{ij} = \frac{\exp\left[-\frac{s_{ij}}{k}\right]}{Z} \quad (4)$$

where, $p^s_{ij}$=The sampling probability of an interaction between a protein atom of type i and ligand atom of type j.

$s_{ij}$=Entropy of interactions between a protein atom of type i and ligand atom of type j.

k=Boltzmann Constant.

Z=Normalization Constant.

The product of $p^e$ from Expression (3) and $p^s$ from Expression (4) gives a relationship between the total probability and gross binding free energy (that is dependent on the interaction model chosen to describe the atomic interactions between the protein and ligand in the protein-ligand complex). This is shown in Expression (5):

$$p_{ij} = p^e_{ij} p^s_{ij} = \frac{\exp\left[-\frac{e_{ij} - Ts_{ij}}{kT_e}\right]}{Z} = \frac{\exp\left[\frac{g^*_{ij}}{kT_e}\right]}{Z} \quad (5)$$

where, $p_{ij}$=The total probability of interactions between a protein of type i and ligand atom of type j.

$p^e_{ij}$=The energetic probability of an interaction between a protein atom of type i and ligand atom of type j.

$p^s_{ij}$=The sampling probability of an interaction between a protein atom of type i and ligand atom of type j.

$e_{ij}$=The energy of the interaction of a protein atom i and ligand j.

$s_{ij}$=Entropy of interactions between a protein atom of type i and ligand atom of type j.

k=Boltzmann Constant.

$T_e$=Experimental temperature at which the data base information is obtained.

Z=Normalization Constant.

The interaction model that is chosen is comprised of an interaction radius and a set of eligible atom types.

Expression (5) can be changed so that it is solved for $g^*_{ij}$, the free energy as set forth in Expression (6). This comprises the quasichemical approximation. Expression (6) is determined from the frequency of observed interactions:

$$g^*_{ij} = -kT_e \log(p_{ij}) - kT_e \log(Z) \quad (6)$$

where, $g^*_{ij}$=The gross free energy of an interaction between a protein atom of type i and ligand atom of type j.

$T_e$=Experimental temperature at which the data base information is obtained.

k=Boltzmann Constant.

Z=Normalization Constant.

$P_{ij}$=The total probability of an interaction between a protein of atom type i and ligand atom of type j.

When the appropriate reference state is selected, the Normalization Constant can be eliminated. The reference state contributes a free energy of $\bar{g}$ to every gross free energy term $g_{ij}^*$. This is shown via Expressions (7), (8), and (9):

$$\bar{g} = -kT_e \log(\bar{p}) - kT_e \log(Z) \quad (7)$$

$$g_{ij} = g^*_{ij} - \bar{g} \quad (8)$$

$$g_{ij} = -kT_e \log\left[\frac{p_{ij}}{\bar{p}}\right] \quad (9)$$

where for Expressions (7), (8), and (9), $\bar{g}$=Gross free energy of the reference state.

$\bar{p}$=The average probability of an interaction between protein and ligand atoms.

$g_{ij}$=Net free energy of the interaction between a protein atom of type i and ligand of type j.

$g^*_{ij}$=The gross free energy of an interaction between a protein atom of type i and ligand atom of type j.

$P_{ij}$=The total probability of an interaction between a protein of atom type i and ligand atom of type j.

$T_e$=Experimental temperature at which the data base information is obtained.

k=Boltzmann Constant.

Z=Normalization Constant.

Expression (9) relates the statistical information about interatomic interactions in the crystal structures of the protein-ligand complex to term by term contributions to binding free energy. The $g_{ij}$ s, when summed, will approximate the complete form of free energy in Expression (1) that is provided at 104.

The correct interaction model and reference state for application of a knowledge-based potential data to a protein-ligand binding event is deducted from the terms in Expression (6) (repeated below:):

$$g^*_{ij} = -kT_e \log(p_{ij}) - kT_e \log(Z) \quad (6)$$

More specifically, changes in the solvation entropy with regard to the complex formation occur because of a gain or loss in the solvent order, which is a correlation between the potential surface of the solvent exposed to atoms in the ligand, protein, or complex. These correlations are generally twice the size of a water molecule beyond the boundary of the ligand, protein, or complex. As the interactions between the ligand and protein result in desolvation, there is a change in the configurational entropy. Thus, to form a particular intermolecular contact between a protein and ligand, each of the atoms in contact must be desolvated. Where there has been a large amount of order destroyed by this process, there is an entropic increase due to the desolvation for the formation of that particular contact.

The selection of the large interaction radius, between the protein and ligand, should be the correlation length of solvent ordering. When this is the case, the probability of the specific contacts observed occurring will include the average effect of the contribution of solvation entropy to the prediction of free energy. As such, the system and method of the present invention will select a large interaction radius for the interaction model. For the purposes of the present invention, the interaction model will define a ligand atom to be in contact with a protein atom if there are within the interaction radius of one another.

Each contact formed involves an energy loss based on desolvation. This s must be accounted for in the reference state. In defining the reference state, the specificity of the loss due to desolvation of the specific contact becomes a general element that is factored in and the remaining energetic contributions in the interaction model with a large interaction radius take into account simply that a loss due to desolvation has taken place.

In selecting the reference state, there is effectively unrestricted spatial sampling of the ligand with respect to the protein. As such, the reference state has no perceived notion of the chemical structure. Thus, the difference between the free estimates of a specific structure and that of the reference state accounts for the loss of configurational entropy in a collection of atoms upon formation of a specific, largely rigid chemical structure. If Expression (8) is now considered $$g_{ij} = g^*_{ij} - \bar{g} \quad (8)$$

in which $\bar{g}$ is subtracted from $g^*_{ij}$, the entropic effect of unrestricted sampling and the effect of desolvation is taken into account.

Using the Expressions set forth above, the system and method of the present invention score and then rank the candidate structures based, in large part, on the determination of the total binding free energy that is defined by Expression (10):

$$\Delta G = \sum_{ij} g_{ij} \Delta_{ij} \quad (10)$$

where, $\Delta G$=The total binding free energy.

$g_{ij}$=Net free energy of the interaction between a protein atom of type i and ligand of type j.

$\Delta_{ij}$=This term is zero unless i and j are within the interaction radius of each other, in which case, it is equal to one.

Using the interaction model and reference state that was previously disussed, ΔG is an approximation to the complete change in free energy in the complex formation. Coarse-graining that was discussed included the entropic effects of solvaion and the reference state has taken into consideration the effects of solvation energy and the configurational entropy. Moreover, according to the system and method of the present invention, a closer look is taken of the atom types and their affect on the energy contributions that really take place in complex formation, not a generalization of the atom types.

To test the accuracy of the approximation of binding free energy, the method of the present invention was compared with experimental measurements of binding free energy. The method for approximating binding free energy according to the present invention was applied to guanine based ligands that had been designed, synthesized, and assayed for purine nucleoside phosphorylase ("PNP"). In Table 5 below, each of the molecules were interactively built using the system and method of the present invention and low energy conformation was found with the conformational search according to the present invention. As such, the molecules were tested as if they had been generated using the de novo growth method of the present invention. In other words, given enough computation time the system and method of the present invention would have generated the listed molecules and any corresponding conformations, even though, undirected generation of these exact ligands is highly improbable. The set of molecules in Table 5 was generated by the system and method of the present invention for correlation between free energies taken as the logarithm of the binding constants or $IC_{50}$ measurement, which is an experimental determination of the propensity for complex formation, and knowledge-based potentials of the present invention:

TABLE 5

Binding Constants vs. Invention Knowledge-Based Potentials for PNP Ligands

| Ligand | Invention Knowledge-Based Potential | $K_i$ or $IC^a_{50}$ ($\mu M$) |
|---|---|---|
| GDP | −13.9 | 1500 |
| GMP | −14.1 | 2000 |
| GTP | −14.7 | 2400 |
| dGDP | −14.9 | 590 |
| dGMP | −14.4 | 1400 |
| 3-(trifluoromethyl)phenymethyl-9-deazaguanine | −12.3 | 0.036[a] |
| acyclovir | −15.8 | 91 |
| pyridin-3-ylmethyl-9-deazaguanine | −18.5 | 0.025[a] |
| 2-hydroxyphenylmethyl-9-deazaguanine | −18.1 | 0.270[a] |
| 4-hydroxyphenylmethyl-9-deazaguanine | −18.7 | 0.260[a] |
| phenylmethyl-9-deazaguanine | −18.7 | 0.051[a] |
| 2-(2-phosphatidylethyl)phenylmethylguanine | −17.8 | 0.035[a] |
| 3-methylphenylmethyl-9-deazaguanine | −19.4 | 0.057[a] |
| 3-methoxyphenylmethyl-9-deazaguanine | −18.1 | 0.082[a] |

The knowledge-based potential data, according to the present invention, correlates well with the experimental binding free energy for over five orders of magnitude in the binding constants. The strong correlations that were found for the binding free energy predictions according to the system and method of the present invention indicate an ability to effect de novo drug design of lead molecules.

The system of the present invention may be operated in one of three modes: automatic, directed, or assisted. In the automatic mode, all that is necessary is to provide the starting protein structure and a coordinate on the protein that is the specific binding site. From that point on, the system will generated ligands with at least one atom within an interaction radius length of the specified coordinate. The directed mode is an interaction method in which the user specifies the molecular fragments which are selected and where they are to bind. The assisted mode starts with the user specifying a fragment. Then, the assisted mode proceeds automatically.

The terms and expressions which are used herein are used as terms of expression and not of limitation. There is no intention in the use of such terms and expressions of excluding the equivalents of the features shown and described, or portions thereof, it being recognized that various modifications are possible in the scope of the present invention.

We claim:

1. A method for building molecules for binding at a receptor site, comprising the steps of:

(a) evaluating a receptor site for a molecular make up of at least a portion of the receptor site to which a molecule being grown will bind and generating at least a coordinate of at least a portion of the receptor site to which the molecule being grown will bind, and outputting, at least with respect to the molecular make up of the receptor site, the coordinate of the portion of the receptor site to which the molecule being grown will bind;

(b) estimating free energy of the molecule being grown using knowledge-based potential data to estimate free energy and outputting the estimated free energy; and (c) building a molecule for binding to the receptor site using the outputs from steps (a) and (b), with the building step including building the molecule by selecting molecular fragments at orientations that will result in free energy estimates for the molecule that may be higher than a lowest free energy estimate possible for the molecule.

2. A method for building molecules for binding at a receptor site, comprising the steps of:

(a) evaluating a receptor site for a molecular make up of at least a portion of the receptor site to which a molecule being grown will bind and generating at least a coordinate of at least a portion of the receptor site to which the molecule being grown will bind, and outputting, at least with respect to the molecular make up of the receptor site, the coordinate of the portion of the receptor site to which the molecule being grown will bind;

(b) estimating the free energy of the molecule being grown using knowledge based potential data to estimate free energy and outputting the estimated free energy, comprising the substeps of:

(1) selecting an interaction radius of a length that negates adverse affects from solvent entropy effects;

(2) developing an accessible listing regarding known structures of molecule/receptor complexes that includes at least molecular fragment (3) developing an accessible listing regarding atom types based on classes of molecular interactions that include at least atom types predicted to interact in the molecule/receptor complex of the molecule being grown and the receptor site;

(4) generating an accessible listing of molecular interactions for known structures of molecule/receptor complexes based on the selection at substep (1) and the listing developed at substeps (2) and (3);

(5) selecting a reference state for the molecule being grown that negates the adverse effects from solvent and configurational entropy effects;

(6) developing a quasichemical approximation for the molecule that is being grown; and (7) generating the estimated free energy of the molecule being grown based on the listing developed at substep (4), the selection at substep (5), and the quasichemical approximation developed at substep (6); and (c) building a molecule for binding to the receptor site using the outputs from steps (a) and (b), with the building step including building the molecule by selecting molecular fragments at orientations that will result in free energy estimates for the molecule that may be higher than a lowest free energy estimate possible for the molecule.

3. The method as recited in claim 2, wherein a molecule can be grown according to steps (a) to (c) in less than 5 seconds.

4. The method for estimating free energy in a molecule being grown for connection at a receptor site in a molecule/receptor complex, comprising the steps of:

(a) selecting an interaction radius of a length that negates adverse affects from solvent entropy effects;

(b) developing an accessible listing of known structures of molecule/receptor complexes that includes at least atom coordinates and corresponding chemical elements;

(c) developing an accessible listing of atom types based on clases of molecular interactions that include at least atom types predicted to interact in the molecule/receptor complex of the molecule being grown and the receptor site;

(d) generating an accessible listing of molecular interactions for known structures of molecule/receptor complexes based on the selection at step (a) and the listing developed at steps (b) and (c);

(e) selecting a reference state for the molecule being grown that negates the adverse effects from solvent and configurational entropy effects;

(f) developing a quasichemical approximation for the molecule that is being grown; and (g) generating the estimated free energy of the molecule being grown based on the listing developed at step (d), the selection at step (e), and the quasichemical approximation developed at step (f).

5. A method for building molecules for binding at a receptor site, comprising the steps of:

(a) evaluating a receptor site for a molecular make up of at least a portion of the receptor site to which a molecule being grown will bind and generating at least a coordinate of at least a portion of the receptor site to which the molecule being grown will bind;

(b) loading at least hydrogen ("H") atoms at least at the portion of the receptor site to which the molecule being grown will bind;

(c) randomly selecting an H atom of the H atoms loading at the receptor site;

(d) randomly selecting a molecular fragment from the predetermined group of molecular fragments and randomly selecting an H atom from the molecular fragment;

(e) forming a bond at the selected H atoms selected at steps (c) and (d);

(f) orienting the molecular fragment with respect to the bond formed at step (e) so that the molecule being grown has low free energy;

(g) estimating free energy for the molecule being grown using knowledge-based potential; and (h) comparing the estimated free energy at step (g) with a free energy estimate of a molecule bound at the receptor site before the fragment was bonded to the receptor site at step (e) to determine if the estimated free energy at step (g) is more or less than a prior estimated free energy for the molecule before the fragment was bonded to he receptor site at site (e), and accepting the addition and orientation of the molecular fragment if the estimated free energy is less and accepting the addition and orientation of the first molecular fragment according to a probability determined in a predetermined manner if the estimated free energy is more.

6. The method as recited in claim 5, wherein step (g) for estimating free energy includes the substeps of:

(1) selecting an interaction radius of a length that negates adverse affects from solvent entropy effects;

(2) developing an accessible listing regarding known structures of molecule/receptor complexes that includes at least atom coordinates and corresponding chemical elements;

(3) developing an accessible listing regarding atom types based on classes of molecular interactions that include at least atom types predicted to interact in the molecule/receptor complex of the molecule being grown and the receptor site;

(4) generating an accessible listing of molecular interactions for known structures of molecule/receptor complexes based on the selection at substep (1) and the listing developed at substeps (2) and (3);

(5) selecting a reference state for the molecule being grown that negates the adverse effects from solvent and configurational entropy effects;

(6) developing a quasichemical approximation for the molecule that is being grown; and (7) generating the estimated free energy of the molecule being grown based on the listing developed at substep (4), the selection at substep (5), and the quasichemical approximation developed at substep (6).

7. The method as recited in claim 5, wherein a molecule can be grown according to steps (a) to (h) in less than 5 seconds.

8. The method as recited in claim 5, wherein orienting the molecular fragment in step (f) includes torsional rotation in fixed increments.

9. The method as recited in claim 8, where the fixed increments for torsional rotation includes fixed increments of 60°.

10. The method as recited in claim 5, wherein the method of comparing and accepting the molecule is according to a metropolis Monte Carlo selection process.

11. The method as recited in claim 5, wherein the probability in step (h) is determined according to:

$$p = \exp\left[-\frac{\Delta g}{T}\right]$$

where, p=Probability of acceptance.

$\Delta g = \Delta G/N$ is the change in free energy per atom (with $\Delta G$ being the free energy difference upon adding the fragment at issue and N being the total number of atoms in the ligand).

T=Temperature.

12. A method for growing molecules for binding at a receptor site, comprising the steps of:
   (a) evaluating a receptor site for a molecular make up of at least a portion of the receptor site to which a molecule being grown will bind and generating at least a coordinate of at least a portion of the receptor site to which the molecule being grown will bind;
   (b) loading at least hydrogen ("H") atoms at least at the portion of the receptor site to which the molecule being grown will bind;
   (c) randomly selecting an H atom of the H atoms loading at the receptor site;
   (d) randomly selecting a molecular fragment from the predetermined group of molecular fragments and randomly selecting a H atom from the molecular fragment;
   (e) forming a bond at the selected H atoms selected at steps (c) and (d);
   (f) orienting the molecular fragment with respect to the bond formed at step (e) so that the molecule being grown has low free energy;
   (g) estimating free energy for the molecule being grown using knowledge-based potential; and
   (h) comparing the estimated free energy at step (g) with a free energy estimate of a molecule bound at the receptor site before the fragment was bonded to the receptor site at step (e) to determine if the estimated free energy at step (g) is more or less than a prior estimated free energy for the molecule before the fragment was bonded to the receptor site at step (e), and accepting the addition and orientation of the molecular fragment if the estimated free energy is less and accepting the addition and orientation of the first molecular fragment according to a probability determined in a predetermined manner if the estimated free energy is more.

13. The method as recited in claim 12, wherein the method further includes repeating steps (c) to (g) for each molecular fragment that is bonded.

14. The method as recited in claim 12, wherein step (g) for estimating free energy includes the substeps of:
   (1) selecting an interaction radius of a length that negates adverse affects from solvent entropy effects;
   (2) developing an accessible listing regarding known structures of molecule/receptor complexes that includes at least atom coordinates and corresponding chemical elements;
   (3) developing an accessible listing regarding atom types based on classes of molecular interactions that include at least atom types predicted to interact in the molecule/receptor complex of the molecule being grown and the receptor site;
   (4) generating an accessible listing of molecular interactions for known structures of molecule/receptor complexes based on the selection at substep (1) and the listing developed at substeps (2) and (3);
   (5) selecting a reference state for the molecule being grown that negates the adverse effects from solvent and configurational entropy effects;
   (6) developing a quasichemical approximation for the molecule that is being grown; and
   (7) generating the estimated free energy of the molecule being grown based on the listing developed at substep (4), the selection at substep (5), and the quasichemical approximation developed at substep (6).

15. The method as recited in claim 12, wherein a molecule can be grown according to steps (a) to (h) in less than 5 seconds.

16. The method as recited in claim 12, wherein orienting the molecular fragment in step (g) includes torsional rotation in fixed increments.

17. The method as recited in claim 16, where the fixed increments for torsional rotation includes fixed increments of 60°.

18. The method as recited in claim 12, wherein the method of comparing and accepting the molecule is according to a metropolis Monte Carlo method.

19. The molecule as recited in claim 12 wherein the probability in step (h) is determined according to $$p = \exp\left[-\frac{\Delta g}{T}\right]$$

where, p=Probability of acceptance.

$\Delta g = \Delta G/N$ is the change in free energy per atom (with $\Delta G$ being the free energy difference upon adding the fragment at issue and N being the total number of atoms in the ligand).

T=Temperature.

* * * * *